(12) United States Patent
Cerni (10) Patent No.: US 7,088,446 B2
(45) Date of Patent: Aug. 8, 2006

(54) OPTICAL MEASUREMENT OF THE CHEMICAL CONSTITUENTS OF AN OPAQUE SLURRY

(75) Inventor: Todd A. Cerni, Mead, CO (US)

(73) Assignee: Particle Measuring Systems, Inc., Boulder, CO (US)

( * ) Notice: Subject to any disclaimer, the term of this patent is extended or adjusted under 35 U.S.C. 154(b) by 388 days.

(21) Appl. No.: 10/749,995

(22) Filed: Dec. 31, 2003

(65) Prior Publication Data

US 2005/0146717 A1    Jul. 7, 2005

(51) Int. Cl.
  G01N 15/02    (2006.01)
  G01J 3/28    (2006.01)
(52) U.S. Cl. .................. 356/335; 356/326; 438/16
(58) Field of Classification Search ........ 356/335–343, 356/300, 319, 326; 438/16; 451/5, 6, 8, 451/41

See application file for complete search history.

(56) References Cited

U.S. PATENT DOCUMENTS

| | | | | |
|---|---|---|---|---|
| 5,563,929 A | * | 10/1996 | Connolly et al. ............ 378/51 |
| 5,710,069 A | * | 1/1998 | Farkas et al. ................ 438/7 |
| 5,993,647 A | * | 11/1999 | Huang et al. ................ 210/87 |
| 6,248,474 B1 | | 6/2001 | Cerni et al. | |
| 6,275,290 B1 | | 8/2001 | Cerni et al. | |
| 6,709,311 B1 | | 3/2004 | Cerni | |
| 6,943,878 B1 | * | 9/2005 | Fisher et al. ................ 356/300 |

* cited by examiner

*Primary Examiner*—Layla G. Lauchman
(74) *Attorney, Agent, or Firm*—Patton Boggs LLP (57) ABSTRACT

An opaque slurry chemical constituent measurement system includes a cross-flow or membrane filter having a porous filter element connected between a global slurry loop and a spectrometer. The opaque slurry particles cannot pass through the filter element but pass through the filter cartridge into the day tank, while the chemical constituent to be measured permeates through the filter element to the spectrometer, where it is measured, and thence to a reservoir. About once every five minutes the porous filter element is reverse flushed for less than a second to clear the filter pores. One to several times per hour, the reservoir is emptied into the day tank. The system provides essentially continuous measurement of the slurry chemical composition, does not consume reagent chemicals, does not create a chemical waste stream, and provides high reliability and low maintenance by preventing the abrasive slurry particles from contacting the fluidic sampling valves.

43 Claims, 4 Drawing Sheets

OPTICAL MEASUREMENT OF THE CHEMICAL CONSTITUENTS OF AN OPAQUE SLURRY

BACKGROUND OF THE INVENTION

1. Field of the Invention

The invention pertains to the field of chemical analysis of opaque slurries, such as chemical mechanical planarization ("CMP") slurries. More specifically, it relates to an optical method of determining the chemical constituents of a CMP slurry.

2. Statement of the Problem

Chemical mechanical planarization (CMP) processes are used to planarize and smooth such surfaces in the integrated circuit and optics industries. CMP has emerged as the preferred method of planarization for manufacture of multiple layer semiconductor wafers having feature sizes less than or equal to 0.35 microns.

CMP is accomplished with a CMP polishing slurry and a complex polishing machine. Since the CMP process usually occurs in many different places in the integrated circuit or optics manufacturing line, generally the CMP slurry is continually pumped around a global distribution loop in the fabrication facility by a CMP slurry dispense module. Each polishing machine taps off the global loop.

CMP process slurries typically consist of a high concentration of sub-micron size abrasive particles, such $SiO_2$, $Al_2O_3$, or $CeO_2$ particles, suspended in a multicomponent liquid solution. The abrasive concentration is generally 4% to 18% solids by weight. $SiO_2$ slurries are referred to in the art as "oxide" slurries, and $Al_2O_3$ slurries are referred to as "metal" slurries. CMP slurry manufacturers attempt to produce slurries that consist predominantly of particles less than 1.0 micron or even 0.5 microns in size.

The multicomponent solution usually includes one or more chemically active agents, such as an oxidizer or an acid or base solution. Since CMP slurries intimately contact the materials out of which the integrated circuit or optics components are made, to achieve repeatable, consistent results, it is important that the chemical content of the slurry be known and controlled. For example, materials that are planarized and chemicals used in integrated circuit manufacturing processes can get into the slurry and affect subsequent layers when they are planarized. Therefore, it is important to be able to periodically check the chemical composition of a CMP slurry. For chemical components that are stable over time, occasional monitoring of the chemical components may be sufficient. However, some chemicals and materials that make up the slurry can decompose over time. For example, most CMP slurries contain an oxidizer, the most common of which is hydrogen peroxide ($H_2O_2$). Hydrogen peroxide is currently included in 80% of all CMP slurries. $H_2O_2$ is unstable and decays over time. It is widely accepted that the $H_2O_2$ concentration in a CMP slurry must be continuously monitored in the global loop. As another example, benzotriazole (BTA) is a copper corrosion inhibitor commonly used in copper CMP slurries. If the concentration of BTA falls outside certain control limits, defects will result. In the past, monitoring of such chemicals as $H_2O_2$ and BTA has been done by analytical chemical means, such as titration. However, such methods are slow, consume approximately ten thousand dollars worth of reagent chemicals each year, and create a hazardous chemical waste stream that requires environmental treatment. Automated titration systems may require thirty minutes to make a measurement. In addition there is a high maintenance requirement due to the exposure of valves and related fluidic components in the titration system to the abrasive slurry.

Recently, the present inventor created a spectrometer system and method for measuring the chemical constituents of a CMP slurry. See United States Patent Publication No. 2003-0032366. However, this system works best in regions of the electromagnetic spectrum in which the scattering and absorption by the slurry is low to moderate. Hydrogen peroxide does not exhibit any significant optical absorption in the visible or near infrared spectral regions in which the above-mentioned system is most effective in the most common slurries. Hydrogen peroxide does exhibit a strong ultraviolet (UV) absorption band at wavelengths less than 300 nanometers (nm). In this spectral region, the abrasive components of common CMP slurries provide little or no optical transmission, such that previously described spectroscopic methods become impractical or impossible. Thus, the above-mentioned spectroscopic system and method is less than ideal for measurement of hydrogen peroxide, particularly when high accuracy is required.

Thus, there remains a need for a system and method for essentially continuous measurement of hydrogen peroxide and other slurry chemical constituents having absorption bands in spectral regions that coincide with very low optical transmission spectral regions of the other slurry components.

SUMMARY OF THE INVENTION

The present invention overcomes the problems outlined above, and advances the art, by providing a system and method that can essentially continuously monitor chemical constituents of an opaque slurry that absorbs radiation primarily in a spectral range in which the slurry is opaque. A liquid sample containing the chemical constituent is continuously separated from the slurry particles as they flow through a separator. The chemical constituent is measured as the sample containing the chemical constituent is flowed through an optical detector, preferably a spectrometer. In the preferred embodiment, the chemical constituent is continuously or essentially continuously separated from the slurry using a filter. Preferably, the sample containing the chemical constituent is drawn through the optical detector into a reservoir, and periodically the reservoir is emptied back into the slurry distribution system. The volume of the liquid sample which is measured via spectroscopic means, to determine its chemical composition, is typically 3 to 5 orders of magnitude smaller than the volume of slurry contained in the slurry distribution system. Recombination of slurry components after spectroscopic measurement, prevents any measurable alteration of the slurry composition in the slurry distribution system. Continuous extraction of liquid from the slurry global loop, without recombination, would eventually cause a measurable change in the composition of the slurry in the global loop. Preferably, the pores of the filter are periodically unplugged by a short, relatively high pressure reverse burst of the sample containing the chemical constituent.

The system provides a method of measuring a chemical constituent of an opaque slurry comprising opaque slurry particles and the chemical constituent, the method comprising: flowing at least a portion of the slurry into a separator; separating the chemical constituent from the opaque slurry particles; flowing the separated chemical constituent into an optical detector; and measuring the chemical constituent while the chemical constituent is flowing through the detector. Preferably, the separating comprises filtering the slurry with a porous filter element. Preferably, the filtering utilizes a membrane or cross-flow filter. Preferably, the method further comprises reverse flushing the separated chemical constituent through the porous filter element. Preferably, the reverse flushing is performed for five seconds or less for each minute of the flowing, more preferably is performed for one second or less for each minute of the flowing, and most preferably is performed for one second or less for each five minutes of the flowing. Preferably, the method further comprises flowing the chemical constituent from the optical detector into a reservoir. Preferably, the method further comprises emptying the reservoir. Preferably, the emptying is performed less than once for each twenty minutes of the flowing. Preferably, the method further comprises recombining the separated chemical constituent and the opaque slurry particles. The recombining comprises, in one embodiment, reverse flowing the chemical constituent in a reverse direction from the direction of the flowing, and in another embodiment, flowing the separated slurry particles and chemical constituent into a tank where they are recombined. Preferably, the flowing of the separated chemical constituent comprises flowing in a downward direction after the separating. Preferably, the flowing into an optical detector comprises flowing the chemical constituent in an upward direction through the optical detector. Preferably, the measuring comprises measuring with a spectrometer. Preferably, the flowing is performed essentially continuously. Preferably, the method includes connecting the separator between the dispense engine and the day tank of a slurry distribution system. The key to higher reliability and lower maintenance lies in the fact that, for this invention, no switching valves are exposed to the abrasive slurry, which is not the case in automated chemical titration systems.

In another aspect, the invention provides a method of measuring a chemical constituent of an opaque slurry comprising opaque slurry particles and the chemical constituent, the method comprising: separating at least a portion of the chemical constituent from the opaque slurry particles; placing the separated chemical constituent into an optical detector; measuring the chemical constituent; and recombining the separated chemical constituent and the opaque slurry particles.

The invention also provides a system for measuring a chemical constituent of an opaque slurry comprising opaque slurry particles and the chemical constituent, the method comprising: a separator for separating the slurry particles from the chemical constituent, the separator comprising a slurry region and a chemical constituent region; an optical detector; and a flow control system for controlling flow of the chemical constituent from the chemical constituent region to the optical detector. Preferably, the separator comprises a filter. Preferably, the separator comprises a membrane or cross-flow filter. Most preferably, the separator comprises a filter selected from the group consisting of a ceramic filter and an inert polymer membrane filter. Preferably, the filter includes a permeate port located at the top of the filter. Preferably, the optical detector includes a flow cell, and the flow control system includes a chemical constituent conduit connected between the permeate port and the bottom of the flow cell. Preferably, the flow control system includes a pressure bleed port. Preferably, the flow control system further includes a valve located between the optical detector and the pressure bleed port. Preferably, the flow control system includes a pressure source and a first valve, and the first valve is located between the pressure source and the optical detector. Preferably, the system further includes a second valve located between the pressure source and the separator. Preferably, the valve is located between the pressure source and the separator. Preferably, the flow control system includes a reservoir connected to the optical detector. Preferably, the system further includes: a chemical constituent return conduit; a first valve connected between the separator and the optical detector, a second valve connected between the optical detector and the reservoir, and a third valve connected between the reservoir and the chemical constituent return conduit. Preferably, the system further includes a fourth valve located between the reservoir and the separator. Preferably, the system further includes a liquid level sensor connected to the reservoir. Preferably, the optical detector comprises a spectrometer. Preferably, the flow control system further controls flow of the separated slurry particles from the slurry region and the control system includes a conduit adapted to connect the separator to a day tank of a slurry distribution system.

In a further aspect, the invention provides a system for measuring a chemical constituent of an opaque slurry comprising opaque slurry particles and the chemical constituent, the method comprising: a filter including a filter input port, a slurry retentate region, and a chemical constituent permeate region; an optical detector; and a flow control system comprising: a conduit connecting the chemical constituent permeate region and the optical detector; and a pressure bleed port connected to the optical detector. Preferably, the optical detector comprises a spectrometer. Preferably, the filter is selected from the group consisting of a ceramic filter and an inert polymer membrane filter.

The present disclosure is described principally in terms of a system for monitoring hydrogen peroxide, but it will be immediately evident that it can be applied to measurement of any chemical constituent of any slurry, and particularly in spectral regions where the slurry is opaque. For example, the system of the invention also is very effective in measuring the concentration of benzotriazole (BTA), a copper corrosion inhibitor that is added to conventional copper CMP slurries. The systems and methods of the invention provide high sensitivity to small changes in the chemical characteristics of the slurry, preferably with autonomous operation in an industrial environment.

The advantages of the invention over the prior art are: (a) lower cost, (b) higher reliability and lower maintenance, (c) no chemical reagent consumption, which contributes to cost of ownership, (d) no chemical waste stream, and (e) continuous measurement versus batch sampling.

DETAILED DESCRIPTION OF THE PREFERRED EMBODIMENT

Figure 1:
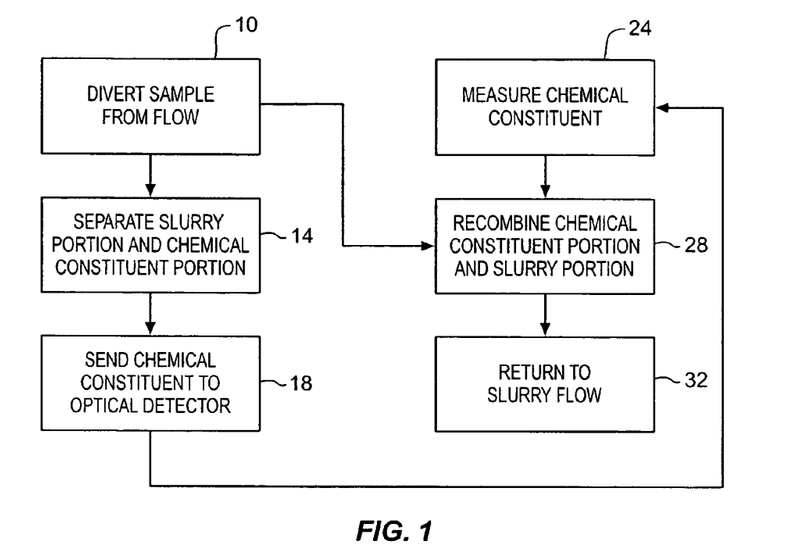
FIG. 1 shows a flow chart of the preferred embodiment of the method according to the invention.

FIG. 1 is a flow chart showing the key processes of the method for measuring the chemical constituents of an opaque slurry according to the invention. First, a sample stream is diverted 10 from a slurry flow, which is preferably the slurry global loop 210 (FIGS. 2–6) in a fabrication facility. The diverted sample then is separated 14 into an opaque portion containing the opaque slurry particles, such as the $SiO_2$, $Al_2O_3$, or $CeO_2$ particles, and a chemical portion containing the chemical constituent or constituents to be measured, such as hydrogen peroxide. The chemical constituent is then sent 18 to the optical detector and the chemical constituent is optically measured 24. The slurry portion and the chemical constituent portion then are recombined 28 and returned 32 to the slurry flow. In the preferred embodiment, the sampling of the slurry flow is essentially continuous during the time that the slurry flow is operating. The term "essentially continuous" means that the sampling can be done continually while the slurry is flowing, except for short periods when the system is being regenerated or reset. For example, in some systems the separator may be flushed for short periods such as a second or less every five minutes. "Essentially continuous" is meant to include such systems. In addition, the invention contemplates that, like most electronic systems, the system of the invention may not always be turned on, or may be programmed to operate only at certain times. "Essentially continuous" includes such variations, as long as when it is on, the system is capable of flowing the sample continuously except for short periods amounting to a minute or less for every hour of operation.

Figure 2:
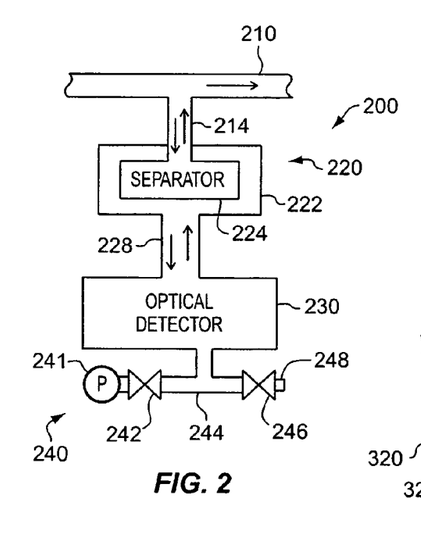
FIG. 2 is a block diagram illustrating one generalized embodiment of an opaque slurry measurement system according to the invention.

FIG. 2 illustrates a simplified chemical constituent measurement system 200 according to one preferred embodiment of the invention. This system illustrates a simple two-way flow system in that the pumps and many of the other elements that control fluid flow in the commercial system have been eliminated to more easily illustrate the most general aspects of the system. System 200 includes a separator 220, an optical detector 230, and a flow control system 240. Flow control system 240 comprises diversion conduit 214, chemical constituent conduit 228, control conduit 244, pressure source 241, return pressure valve 242, pressure relief valve 246, and pressure bleed port 248. System 200 is connected to slurry global supply line 210 via diversion conduit 228. Separator 220 includes a slurry opaque particle region 224 and a chemical constituent region 222. In the preferred embodiments, a filter or permeable membrane separates the regions 224 and 222, though other separation mechanisms, such as a spin separator, may be used. Control conduit 244 is connected between optical detector 230 and valves 242 and 248. Valve 242 is connected between pressure source 242 and control conduit 244, while pressure relief valve 246 is connected between control conduit 244 and pressure bleed port 248. In the embodiment 200, the optically opaque slurry particles remain on the side of separator 220 connected to slurry line 210. As indicated by the downward pointing arrow in conduit 228, during one portion of a measurement cycle, valve 242 is closed, valve 246 is open, and the chemical constituent(s) flow through the separator to the optical detector because port 248 is at ambient pressure that is lower than the pressure in loop 210.

In a regeneration cycle, valve 246 is closed and valve 242 is open and the chemical constituent(s) return to separator 220, as indicted by the upward pointing arrow in conduit 228 because the pressure of pressure source 241 is higher than the pressure in slurry line 210. During the regeneration period, the chemical constituents are forced back through separator 220, mix with the opaque slurry particles that remained behind, and the recombined slurry returns to global slurry flow line 210 as indicated by the upward pointing arrow in diversion conduit 214. Preferably, the return flow during the refresh cycle is significantly faster than the inward flow.

Figure 3:
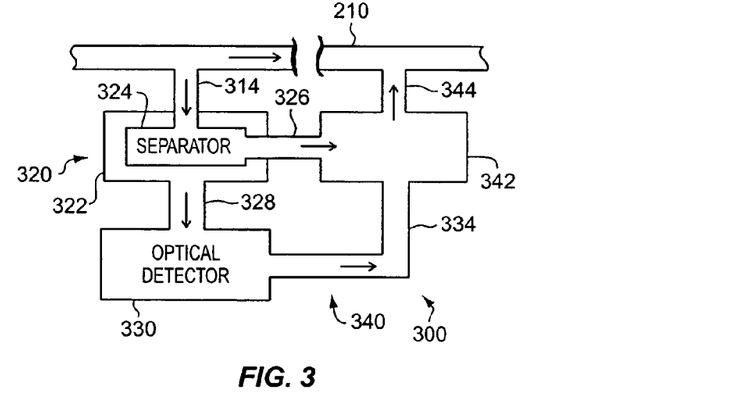
FIG. 3 is a block diagram illustrating an alternative generalized embodiment of an opaque slurry measurement system according to the invention.

In FIG. 3, a second simplified embodiment 300 of the system of the invention is illustrated. Again, in FIG. 3, many of the valves and other elements that direct fluid flow in the commercial system have not been included. System 300 includes separator 320, optical detector 330, and flow control system 340. Flow control system 340 includes diversion conduit 314, opaque slurry particle return conduit 326, inlet chemical constituent conduit 328, outlet chemical conduit 334, recombining chamber 340, and slurry return conduit 344. System 300 is connected to global slurry loop 210 through diversion conduit 314 and return conduit 344. As long as the pressure at the point where diversion conduit 314 connects to global loop 210 is at a pressure sufficiently higher than the pressure at the point where return conduit 344 connects to global loop 210 to drive the constituent and slurry through separator 320, system 300 will work. For example, if the point where diversion conduit 314 is close to or attached to the dispense engine (FIG. 5) and return conduit is close to or empties into the day tank, the dispense engine can provide sufficient pressure to drive the system 300. In this arrangement, conduit 344 acts as a pressure bleed port in that it bleeds pressure from detector 330 allowing the chemical constituent to flow into the detector. System 300 does not have to be regenerated, because the opaque slurry particles flow continuously through opaque particle portion 324 of separator 320 into recombining chamber 340. Likewise, the chemical constituent flows continuously through optical detector 330 into recombination chamber 340. While separator 320, optical detector 330, and recombination chamber 340 are shown in FIG. 3 as individual blocks, in some embodiments, they may simply be different portions of a continuous conduit. For example, recombination chamber 340 may be simply a continuation of conduit 326 or 334. Likewise, flow return path 344 can take many forms, such as a return directly to global supply line 210 or a return to global supply line 210 via a day tank from which the global flow originates.

FIGS. 2 and 3 are intended to illustrate that the flow of the invention as described in FIG. 1 can take on alternative forms. They are intended to be illustrative and not limiting, in that many other flow systems may be used. The system of FIG. 2 is a batch mode sampler system in that it samples a batch of chemical constituent, then returns it to the slurry distribution system, while the system of FIG. 3 is a continuous mode system in that it samples essentially continuously over periods that are very long as compared to the measurement time. However, it should be noted that even in batch mode system 200, the system according to the invention makes the measurement as the chemical constituent is flowing through the spectrometer. Thus, in contrast to the prior art systems, the measurement is available to the user before the sampling is completed, and well before the batch is returned to the slurry distribution system. In prior art titration systems, the user must wait until a batch is sampled and then treated before any measurement is available.

Figure 4:
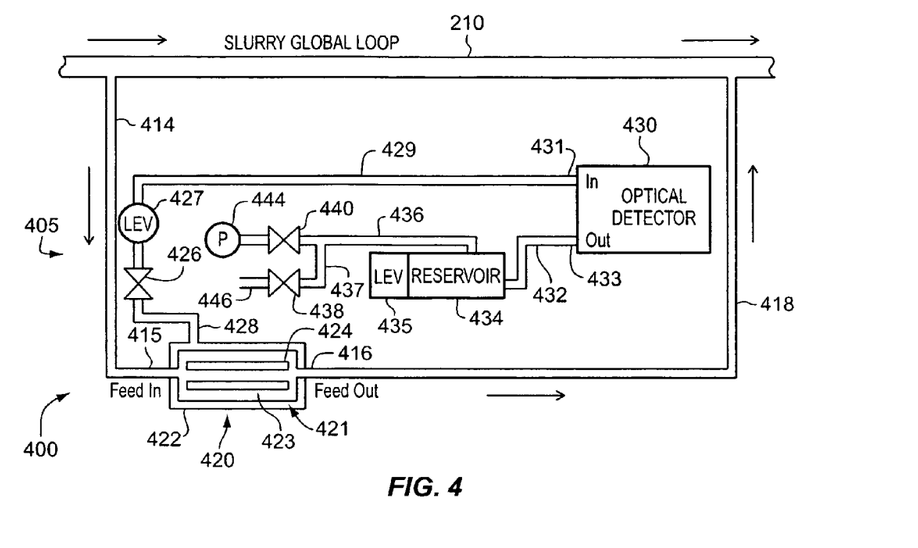
FIG. 4 is a block diagram of a preferred embodiment of an opaque slurry chemical constituent measurement system according to the invention.

FIG. 4 shows a preferred embodiment of a chemical constituent measurement system 400 according to the invention. System 400 includes separator 420, optical detector 430, and flow control system 405. Flow control system 405 includes diversion conduit 414, reservoir 434, pressure source 444, valves 426, 438, and 440, liquid level sensors 427 and 435, chemical constituent conduits 429, 432, 436, and 437, and pressure bleed port 446. Flow control system 405 also includes a controller electronic subsystem 700 and related elements that will be discussed in connection with FIG. 7 below. System 400 is connected to global slurry loop 210 via conduits 414 and 418. Inlet 416 of separator 420 is connected to global slurry loop 210 via diversion conduit 414, while separator outlet 416 is connected to global slurry loop 210 via return conduit 418. Chemical constituent port 428 of separator 420 is connected to inlet 431 of optical detector 430 via valve 426, liquid level sensor 427, and chemical constituent conduit 429. Reservoir 434 is connected to outlet port 433 of optical detector 430 via chemical constituent conduit 432. Liquid level sensor 435 measures the level of liquid in reservoir 434. Reservoir 434 is connected to pressure bleed port 446 via conduits 436 and 437 and valve 438 and to pressure source 444 via conduit 436 and valve 440. Preferably, a leak detector (not shown) with double containment is also incorporated into system 400 and configured with the controller to shut down the sampling procedure in the event of a leak. For some slurries, particularly alumina and cerium slurries, separator 420, 520 should preferably be oriented vertically rather than horizontally as shown in the drawing, to eliminate particle settling within the separator.

Preferably, separator 420 comprises filter 420 comprising a bundle 421 of hollow tubes 423 mounted in a housing 422. Each tube 423 is preferably made of a permeable membrane, such as an inert polymer. In one preferred embodiment, filter 420 is a Pall ACP-1050 hollow fiber membrane filter. Optical detector 430 may be any suitable optical detector that can accurately detect the chemical constituent of interest. In embodiment 400, as well as the other embodiments described herein, the preferred detector 430 is a detector as described in U.S. patent application Ser. No. 09/928,948 filed on Aug. 13, 2001 in the name of Todd A. Cerni, which is hereby incorporated by reference as though fully disclosed herein. The preferred optical detector 430 is sold by Particle Measuring Systems, Boulder Colo. as the SlurryAlert product. For systems intended to measure hydrogen peroxide, the SlurryAlert-BTA CMP chemical monitor is preferred. In this embodiment, as well as the other embodiments described herein, a normally closed valve, such as valves 426 and 440, are preferably Parker Model PV-10-6124-10 valves, while normally open valves, such as valve 438, are normally open Parker Model PV-10-6224-10 valves. In embodiment 400, as well as the other embodiments herein, the liquid level sensors can be any liquid level sensor known in the art. Preferably, they comprise an LED and two photo transistors connected to the system electronic controller (FIG. 7) and located in a manner so as to sense a liquid meniscus. Such liquid sensor designs are well-known in the art and will not be discussed in further detail herein. Pressure source 44 is preferably a clean, dry air source, such as a pressure tank with a conventional regulator.

Chemical constituent measurement system 400 operates as follows. As known in the art, slurry global loop 210 is maintained at a pressure above ambient, which pressure may vary over time, particularly when the pump pressurizing global slurry loop 210 is a slow pump. Initially, valves 426, 438, and 440 are closed. Valve 438 is opened to place conduits 437, 436, and 432 and reservoir 434 at essentially ambient pressure. Valve 426 then is opened. This global loop pressure maintains a gage pressure of 1–3 atmospheres within the interior of tubes 423, which is conventionally called the retentate side. Exterior 424 of tubes 423, which is conventionally called the permeate side, is at near ambient pressure, which forces the liquid portion of the slurry though the membrane from the retentate side to the permeate side. The liquid portion of the slurry is tapped off the top of separator 420, which reduces the chance of gas being trapped in the liquid. That is, as the liquid is driven out of tubes 423, it collects at the bottom of housing 422, and only begins to flow out of the housing when the housing is full. If it were tapped off the bottom of the housing, a mixture of liquid and gas would flow into the chemical constituent conduits. The liquid flows through liquid sensor 427 and conduit 429 into optical detector 430, and thence through conduit 432 into reservoir 434. The chemical constituent or constituents of the liquid are measured by optical detector 430 until liquid level sensor 435 signals that reservoir 434 is full. The minimum size of reservoir 434 is selected so that the measurement time for the optical sensor is sufficient and the maximum size is selected so that only an insignificantly small portion of the total slurry is removed from the global loop in a measurement cycle. Typically, the reservoir size is about 250 milliliters (ml). The flow into the reservoir is about 5 ml per minute to 10 ml per minute, which provides a sample time of about 25 minutes to 50 minutes. The measurement time is significantly shorter. It is noted that separator 420 includes an intrinsic small reservoir in space 424 between membrane tubes 423 and housing 422. Reservoir 434 should be five to ten times larger than this intrinsic membrane separator reservoir to limit the amount of cross contamination between successive sample periods.

It is noted that system 400 is designed so that the flow of slurry into separator 420 is about 5 ml to 10 ml per minute, as compared to a flow of the slurry in the global loop of from about 1 gallon to 10 gallons per minute. Thus, the sample of slurry removed and the retentate returned to the global loop during the sampling process will be very small compared to the total slurry flowing in the global loop. Thus, the increase in concentration of the slurry at the exit of return conduit 418 is, at most, less than a quarter of one percent, which is less than normal concentration fluctuations in the slurry. Moreover, a more likely figure for the increase of concentration is about 0.025 percent.

When level sensor 435 signals that reservoir 434 is sufficiently full, valve 438 closes and valve 440 opens. This starts the regeneration period. Generally, the pressure of pressure source 444 is set to empty reservoir 434 in a minute or less, more preferably in ten seconds or less, and most preferably in five seconds or less. The pressure of pressure source 444 is adjustable, and the required pressure is determined by the pressure in the global loop. That if, if the pressure of pressure source 444 is higher than the pressure of global loop 210, the sampled liquid is forced back through membrane filter tubes 423, and the liquid, mixed with any retentate in separator 420, is forced back into slurry global loop 210. When liquid sensor 427 signals that all liquid has been purged from the permeate side of system 400, valves 440 and 426 close to complete a sampling and regeneration cycle.

Figure 5:
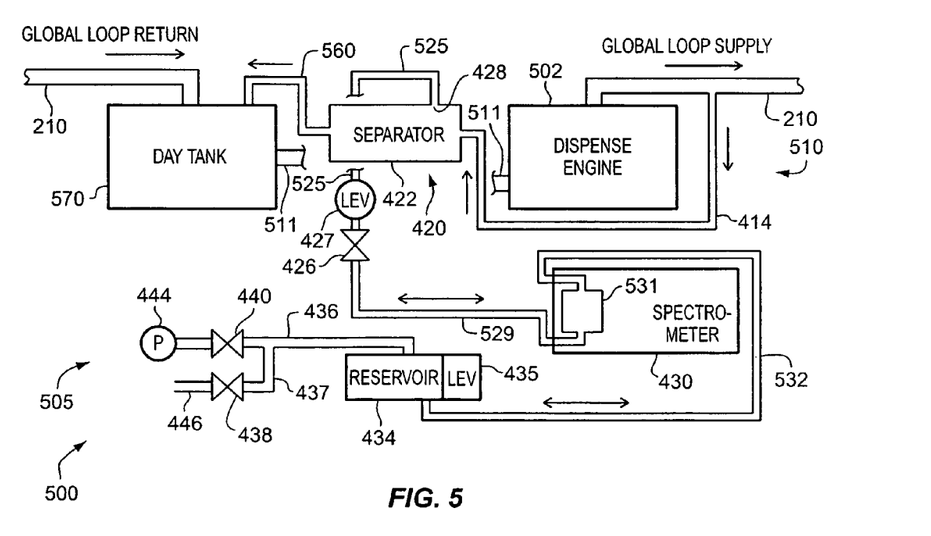
FIG. 5 is a block diagram of a more preferred embodiment of an opaque slurry chemical constituent measurement system according to the invention.

Turning to FIG. 5, an alternative embodiment 500 of the system according to the invention is shown. System 500 is similar to system 400, except that flow control system 505 has been modified and the elements are arranged differently with respect to slurry global loop 210. Elements of system 500 that are the same as those of system 400 are labeled with the same numerals. In FIG. 5, dispense engine 502 and day tank 570 of a typical slurry distribution system 510, as well as global loop 210, are shown. The slurry is sampled via a diversion conduit 414 as before. However, in this system, the retentate flows through return conduit 560 to day tank 570. Dispense engine 502 derives its slurry from day tank 570 via conduit 511. Since the volume of day tank 570 is 50 gallons to 200 gallons, which is much greater than the volume of global loop 210, this results in the retentate having even a smaller impact on the overall concentration of the slurry in loop 210. Preferably, the entrance to diversion conduit 414 is close to the dispense engine so that the full pressure of the dispense engine is available to drive the flow through separator 420. In a conventional slurry distribution system, day tank 570 and dispense engine 502 are located close to each other, which means that the length of conduits 414 and 560 to connect system 500 between the two can remain reasonably small. In conventional slurry distribution systems made by Kinetics™, the day tank is at ambient pressure and the dispense engine outputs slurry at 10 psi to 20 psi. In conventional slurry distribution systems made by BOC™, the day tank is pressurized, and the dispense engine outputs slurry at 30 psi to 50 psi. The system of the invention operates effectively with both slurry distribution systems. The position of the elements in the embodiment of FIG. 5 is altered so that optical detector 430, which is indicated to be a spectrometer, is below separator 420, and enters spectrometer flow cell 531 from the bottom. Flow cell 531 is illuminated to measure the constituent. This permits the permeate to flow down to the spectrometer under gravity, and causes any air or other gas in the liquid permeate that may enter the flow cell to rapidly rise out of it. If the liquid flowed downward in the flow cell, the gas is dragged in a direction opposite to the direction gravity causes it to move; thus, it may be trapped in the flow cell for a longer period. Because of the different orientation of separator 420 and optical detector 430, the positions of level sensor 427 and valve 426 are reversed. Other than the above, the design and operation of system 500 is the same as system 400.

Figure 6:
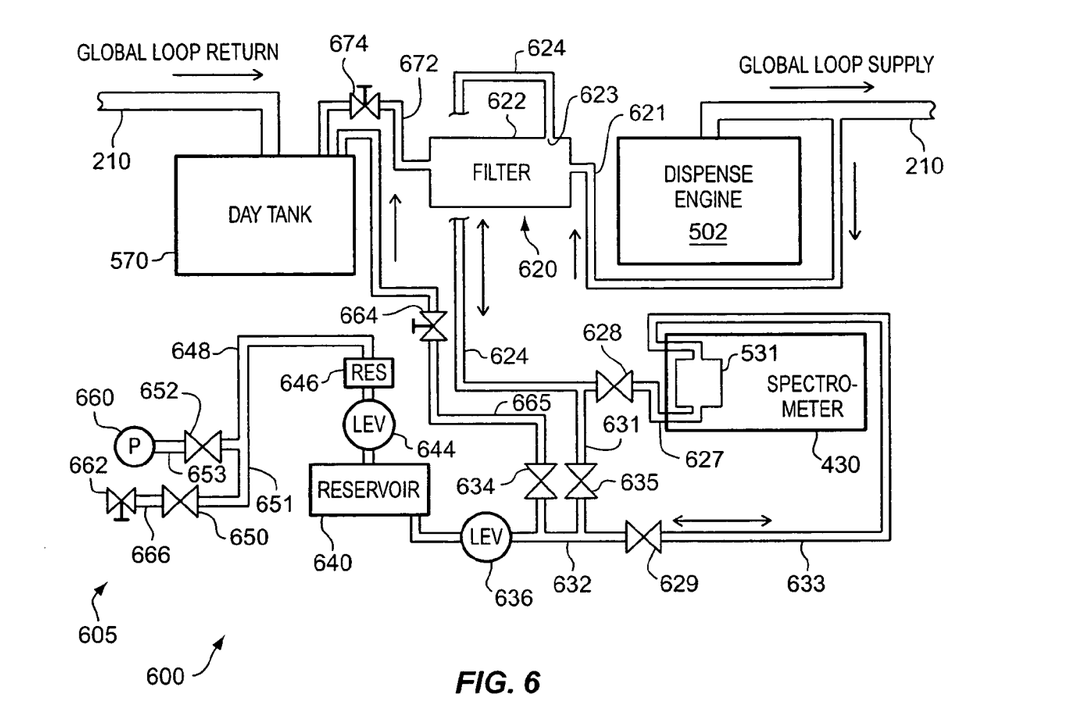
FIG. 6 is a block diagram of the most preferred embodiment of an opaque slurry chemical constituent measurement system according to the invention.

The most preferred embodiment 600 of the opaque slurry chemical constituent measurement system according to the invention is shown in FIG. 6. The dispense engine 502 draws from the day tank 570, as shown in FIG. 5, though this is not shown to in order to not further complicate the figure. System 600 samples the slurry more continuously than systems 400 and 500. Opaque slurry chemical constituent measurement system 600 includes separator 620, detector 430, and flow control system 605. Separator 620 is preferably a filter as described in reference to FIG. 8 below. Optical detector 430 is preferably a spectrometer as described above. Flow control system 605 includes reservoirs 640 and 646, pressure source 660, liquid level sensors 636 and 644, valves 628, 629, 634, 635, 650, and 652, adjustable orifices 662, 664, and 674, conduits 621, 624, 627, 631, 633, 637, 648, 651, 653, 666, and 672, and an electronic controller subsystem 700 as described in FIG. 7 below. In system 600, separator 620 is placed between dispense engine 502 and day tank 570 with the only difference being that an optional adjustable orifice 674 is placed in series with return conduit 672. As before, filter 620 is located between the dispense engine and the day tank to ensure that there is sufficient pressure to drive flow through the filter. If the pressure drop across the filter is too large, then orifice 674 can be closed sufficiently such that the filter does not divert too much of the dispense engine's output. Alternatively, if the pressure drop across the filter is sufficiently small, the filter may be located in a side stream, in parallel with the global loop, at the dispense engine.

In system 600, as in system 500, separator filter 620 is tapped from the top via conduit 624, which connects to lower input line 627 of flow cell 531 of spectrometer 430 via valve 628. Output conduit 633 from the spectrometer connects to reservoir 640 via valve 629. A liquid level sensor 636 is also connected in series with reservoir 636 and valve 629. Valves 628 and 629 are controlled by the same pilot valve (FIG. 7), so they operate in unison. Conduit 631 in series with valve 635 connects spectrometer input conduit 624 and portion 632 of output conduit 633 between valve 629 and reservoir 640. Conduit portion 632 is also connected to the day tank via valve 634 and chemical constituent return conduit 661 in series. Adjustable orifice 664 is also connected in series with conduit 661 on the day tank side of valve 634. As in embodiment 500, the upper side of reservoir 640 is connected to pressure source 660 through valve 652 and to ambient pressure port 666 via valve 650. Liquid level sensor 644 and, optionally, a small overflow reservoir 646 are connected in series along conduit 648. An adjustable orifice 662 is optionally connected to exit port 666. All valves are normally closed, except valve 650, which is normally open to relieve pressure on the system.

System 600 operates as follows. The sampling sequence begins with ambient pressure valve 650 opening, then valves 628 and 629 open together. This places the sampling system at ambient pressure and allows permeate to flow from cross-flow filter 620, through spectrometer 430, to reservoir 640. Orifice 662 may be adjusted to reduce evaporation from reservoir 640. Since spectrometer sample cell 531 fills from the bottom, initial air in the cell is automatically purged and exits the system at port 666. Bubbles are prevented from entering the sample cell by utilizing top permeate port 623 of cross-flow filter 620. Liquid level sensor 644 signals that reservoir 640 is full. Valves 628, 629, and 650 then close. Small overflow reservoir 646 may be used to collect any possible overflow above sensor 644, though in the preferred embodiment this reservoir is not used. At this point, the operating sequence branches to either the filter flush sequence or to the reservoir empty sequence. Filter flush is accomplished asynchronously, after a set time delay.

It is necessary to occasionally reverse flush filter 520, to prevent the pores from clogging with slurry. A sub-second reverse pressure burst, applied every five minutes, prevents the filter from clogging. The duration of the reverse pressure burst should be sufficiently short that only a small amount of fluid will be injected back into slurry global loop 210, and is preferably about 0.25 seconds to 0.5 seconds. All valves are closed at the beginning of the filter flush sequence. Filter reverse flush is accomplished by first opening 652, then quickly opening and closing flush valve 635. Pressure source 660, a regulated supply of clean dry air, provides the pressure for the flush. Valves 628 and 629 remain closed to protect spectrometer sample cell 531 from the short burst of relatively high pressure. Valve 652 then is closed and the system returns to sampling as described above.

Turning now to the reservoir empty sequence, initially, all valves close. Valve 652 then opens, followed by reservoir empty valve 634 opening. This allows reservoir 640 to empty into the day tank within a couple of seconds, even if the day tank is at a pressure above ambient. It may be desirable to place a restriction, such as adjustable orifice 664, in conduit 661 leading to day tank 570, if the fluid surge driven by pressure source 660 is too fast. If the reservoir fill rate is 5 ml/min. to 10 ml/min., then a reservoir of 250 ml capacity would only need to be emptied for a few seconds once very 25 minutes to 50 minutes. When level sensor 636 signals that reservoir 640 is empty, valve 634 and 652 close and the system returns to sampling as described above.

Figure 7:
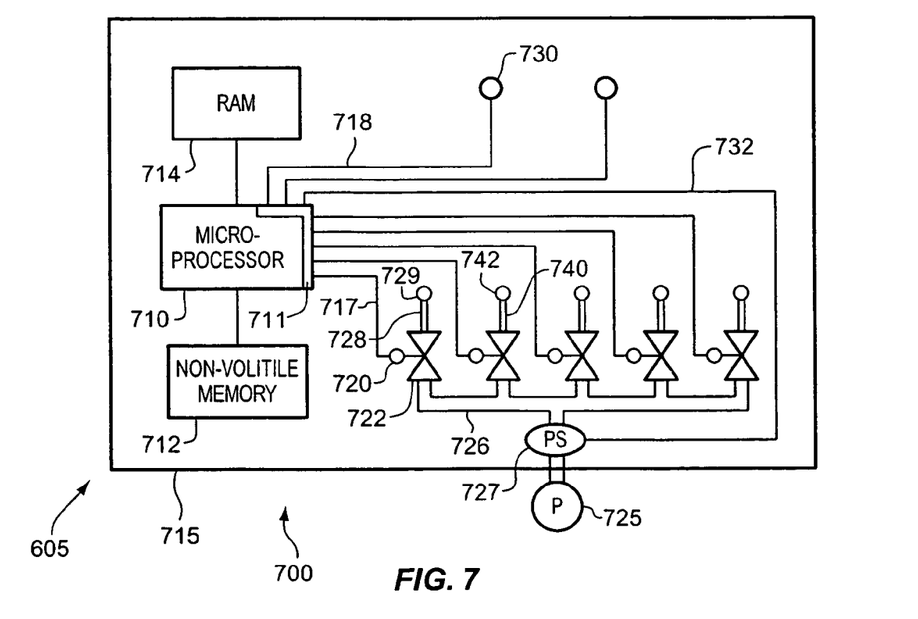
FIG. 7 is a block diagram of the electronics side of the system board of the embodiment of FIG. 6.

Each of the embodiments of system 400, 500, 600 according to the invention discussed above also include a controller electronic subsystem which is part of the flow control system 405, 505, 605. The principal elements of controller electronic subsystem 700 for the most preferred embodiment 600 are shown in FIG. 7. The controller subsystems for the other embodiments are similar and can be designed from this disclosure by those skilled in the art. Controller subsystem 700 is preferably mounted on a board 715. The components discussed in FIG. 6 are preferably mounted on the other side of board 715 from the controller subsystem components. Controller subsystem 700 includes a microprocessor 710, a random access memory (RAM) 714, a non-volatile memory 712, five electronically controlled pilot valves, such as 722, a power transistor 720 associated with each pilot valve 722, a pressure sensor 727, and associated electronic elements as known in the controller art. RAM 714 and non-volatile memory 712 are electrically connected to microprocessor 710 as known in the art. Each pilot valve is connected to a source 725 of pressurized gas, preferably, clean, dry, compressed air, via conduit 726. Pressure sensor 727 is fluidly connected to conduit 726 and electronically connected to parallel port 711 of microprocessor 710 via line 732 to enable the controller to determine if there is enough gas pressure to operate the pilot valves. The controller is programmed to shut the system down if there is not enough pressure. A gas conduit, such as 728, connects one pilot valve with valves 628 and 629 on the other side of board 715 via a feed-through, such as 729. Each of the other pilot valves, such as 742, is connected to one of the other diaphragm valves, 634, 635, 652, or 650 on the other side of board 715 via a corresponding feed-through, such as 729. Each of valves 722, 740, etc., is connected to a power transistor, such as 720, which is in turn connected to microprocessor 710 parallel port 711. Likewise, microprocessor 710 parallel port 711 is connected to each of liquid level sensors 636 and 644 via a feed through, such as 730.

The above design places all of the electronics except for the level sensors on one side of board 715 and all of the liquid carrying components on the other side. Thus, a liquid leak has less chance of creating problems with the electronics. Each diaphragm valve 628, 629, 634, 635, 650, and 652 on the liquid side of the board is driven by compressed air which is electronically controlled via one of pilot valves 722.

In the preferred embodiment, microprocessor 710, non-volatile memory 712, and RAM 714 are part of a PMS CLS-700 controller, available from Particle Measuring Systems, Boulder, Colo. On this controller, the microprocessor is an Intel 8088. Controller subsystem 700 is completely programmable to control sequence timing as desired and to change sequence timing under pre-programmed conditions.

Preferably, in the embodiments discussed above, sample cell 531 is operated at ambient pressure, with essentially continuously flowing liquid sample. In embodiment 600, the continuous flow is only interrupted for less than 1 second every 5 minutes to reverse flush the filter, or a couple of seconds every 10–20 minutes to empty the reservoir. This simplifies calibration, which need not be done over a range of pressures, and need not attempt to compensate for instrumental heating of a stagnant fluid sample. The SlurryAlert 430 wide sample cell 531 has a volume of approximately 2.5 ml, which means that a permeate flow rate of 5 ml/min to 10 ml/min will flush the cell in 0.25 minutes to 0.50 minutes, which supports a measurement interval of less than or equal to one minute. With a sampling system volume of 0.1 liter, and a day tank volume of 200 liters–800 liters, extraction of the liquid portion of the slurry will increase the abrasive content of the slurry by only 0.012% to 0.05%, which is so small as to be unmeasurable.

Controller subsystem 700 is programmed to time how long it takes to fill reservoir 640, using the signals from liquid level sensors 636 and 644. If the time is longer than a predetermined time, the controller will automatically extend the time of the reverse flush. For example, if in a particular setup the reservoir should take ten minutes to fill, but is timed at 20 minutes, the reverse flush time will be extended to a full second.

Figure 8:
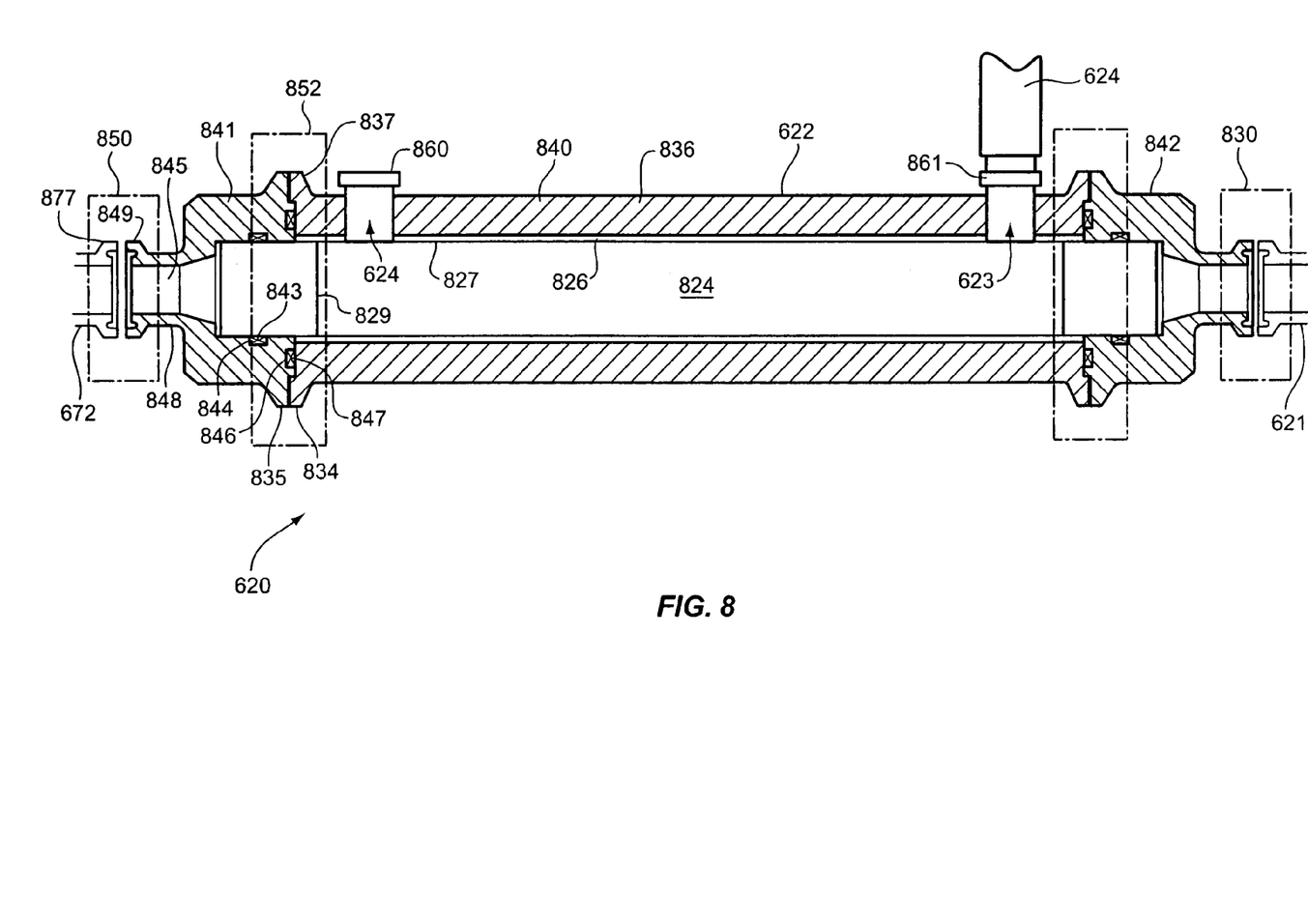
FIG. 8 is a cross-sectional view of the filter of the embodiment of FIG. 6.

FIG. 8 shows the preferred separator, cross-flow filter 620, according to the invention. Filter 620 comprises a filter housing 622 and a filter element 827. Filter housing 622 includes a main housing body 840 and two end caps 841 and 842. Filter element 827 includes a central porous portion 824 and solid end portions 829. Preferably, it is in the form of a hollow cylinder. O-rings 846 fit in a groove 847 in the end caps and provide a seal between the end caps 841 and 842 and the main housing body 840, and O-rings 844 fit in a groove 843 in the end cap and provide a seal between the end cap and solid filter element portions 829. Main housing body 840 preferably includes a hollow cylindrical main portion 836 that widens to a flange 837 at each end, and includes two threaded ports 623 and 624. Preferably, one port is plugged with a screw-in plug 860 and the other port is fitted with a screw-in connector fitting 861 adapted to connect to conduit 624. Each end cap preferably includes a flange 846 at one end and narrows to a neck 848 and then widens to a flange 849. The end caps 841 and 842 are preferably fastened to main body 840 with clamps 852, which are not shown in detail so as not to obscure the details of the filter. End flanges 849 of end caps 841 and 842 are connected to mating flanges 877 of conduits 672 and 621, respectively, via clamps 850 and 830, respectively. Assembly of the parts as described above results in a small gap 826 between the outer circumference of filter element 827 and the inner circumference of housing main body portion 836.

Preferably, housing 622 is made of polypropylene, but it may be made of any suitable, chemically inert plastic or other suitable material. Filter element 827 is preferably made of a ceramic, most preferably alumina ($Al_2O_3$) and zirconium oxide ($ZrO_2$). Preferably, filter element 827 has an outside diameter of 25 mm (0.948 inches) and a length, including the solid portions 829, of 250 mm (9.843 inches). Gap 826 is 1.5 mm (0.06 inches). The other parts are made of conventional materials known in the art.

A prototype opaque slurry chemical constituent measurement system essentially as described above with a Wilden™ pump used to simulate a dispense engine set at 30 psi air pressure, creating an oscillating Klebosol 30N50 slurry pressure of 0 psi-15 psi, but utilizing a Pall ACP-1050 hollow fiber membrane filter 420 as described in connection with FIG. 4, resulted in a permeate liquid flow rate of 6 ml/min. A recent test with a custom ceramic filter 620 had similar results. The permeate flow rate is expected to double if slurry distribution system 510 includes a slurry pressure damper to accomplish a steady 15 psi slurry pressure. Higher global loop 210 pressure, such as in the 50 psi BOC systems, will yield proportionally higher permeate flow rates.

It is a feature of the invention that the slurry can be monitored essentially continuously; that is, the flow is interrupted for less than thirty seconds per hour, and more preferably less than twenty seconds per hour, and most preferably, less than ten seconds per hour.

It is a feature of the invention that separator 420, 520, 620 is plumbed in parallel with global loop 210 such that no valve of the system is in contact with the abrasive slurry particles. This design eliminates serious maintenance problems common to the prior art. A factor that makes this design workable is that separator 420, 520 620 does not present a significant impediment to the flow in global loop 210.

It is a feature of the invention that the five major shortcomings of the prior art opaque slurry chemical constituent measurement systems are overcome. The system according to the invention is less complex; thus, some of the high cost of prior art systems is avoided. The fluid portion of the system isolates all of the valves and major fluidic components from the abrasive slurry. In addition, the optical detectors employed are designed for twelve months of continuous, maintenance-free operation. Thus, the system according to the invention as a whole avoids the high maintenance requirements of the prior art. There is no chemical reagent consumption, which reduces cost of ownership as compared to the prior art. Nor is there any chemical waste stream that must be environmentally handled.

The above-described methods and apparatus for detecting the chemical composition of a slurry are superior to analytical chemical methods and apparatus, such as titration, because they do not consume chemicals, do not create a hazardous chemical waste stream, and are much faster. With response times of 1 minute to 10 minutes from the beginning of a sample cycle to a completed measurement, the methods and apparatus of the invention provide much better process control than do analytical chemical methods and apparatus, which have response times on the order of 30 minutes at best. In addition, none of the valves or other critical components of the system are exposed to the abrasive slurry components; thus, these components do not wear near as much as the components of the prior art titration systems.

There has been described a method and apparatus for optically measuring the chemical constituents in an opaque slurry, such as a CMP slurry. It should be understood that the particular embodiments shown in the drawings and described within this specification are for purposes of example and should not be construed to limit the invention which will be described in the claims below. For example, the system of FIG. 2 would work even if flow control system 240 included only pressure relief port 248, though many of the advantages of the preferred embodiments would be lost. Further, it is evident that those skilled in the art may now make numerous uses and modifications of the specific embodiments described without departing from the inventive concepts. For example, either of the filters described may be used with any of the embodiments described. The various elements may be arranged differently, and the various processes of the method may be performed in a different order. It is also evident that equivalent structures and processes may be substituted for the various structures and processes described. Consequently, the invention is to be construed as embracing each and every novel feature and novel combination of features present in and/or possessed by the opaque slurry measurement systems and methods described.

The invention claimed is:

1. A method of measuring a chemical constituent of an opaque slurry comprising opaque slurry particles and said chemical constituent, said method comprising:

flowing at least a portion of said slurry into a separator;

separating said chemical constituent from said opaque slurry particles;

flowing said separated chemical constituent into an optical detector; and measuring said chemical constituent while said chemical constituent is flowing through said detector.

2. A method as in claim 1 wherein said separating comprises filtering said slurry with a porous filter element.

3. A method as in claim 2 wherein said filtering comprises filtering with a filter selected from the group consisting of a filter membrane and a ceramic filter element.

4. A method as in claim 3 and further comprising reverse flushing said separated chemical constituent through said porous filter element.

5. A method as in claim 4 wherein said reverse flushing is performed for five seconds or less for each minute of said flowing.

6. A method as in claim 4 wherein said reverse flushing is performed for one second or less for each minute of said flowing.

7. A method as in claim 4 wherein said reverse flushing is performed for one second or less for each five minutes of said flowing.

8. A method as in claim 1 and further comprising flowing said chemical constituent from said optical detector into a reservoir.

9. A method as in claim 8 and further comprising emptying said reservoir.

10. A method as in claim 9 wherein said emptying is performed less than once for each ten minutes of said flowing.

11. A method as in claim 9 wherein said emptying is performed less than once for each twenty minutes of said flowing.

12. A method as in claim 1 and further comprising recombining said separated chemical constituent and said opaque slurry particles.

13. A method as in claim 12 wherein said recombining comprises reverse flowing said chemical constituent in a reverse direction from the direction of said flowing.

14. A method as in claim 12 wherein said recombining comprises flowing said separated slurry particles and chemical constituent into a tank where they are recombined.

15. A method as in claim 1 wherein said flowing said separated chemical constituent comprises flowing in a downward direction after said separating.

16. A method as in claim 1 where said flowing into an optical detector comprises flowing said chemical constituent in an upward direction through said optical detector.

17. A method as in claim 1 wherein said measuring comprises measuring with a spectrometer.

18. A method as in claim 1 wherein said flowing is performed essentially continuously.

19. A method as in claim 1 and further including connecting said separator between the dispense engine and the day tank of a slurry distribution system.

20. A method as in claim 1 wherein said flowing, separating, flowing and measuring are accomplished without ever contacting said slurry to a fluid valve.

21. A method of measuring a chemical constituent of an opaque slurry comprising opaque slurry particles and said chemical constituent, said method comprising:

separating at least a portion of said chemical constituent from said opaque slurry particles;

placing said separated chemical constituent into an optical detector;

measuring said chemical constituent; and recombining said separated chemical constituent and said opaque slurry particles.

22. A method of measuring a chemical constituent of an opaque slurry comprising opaque and abrasive slurry particles and said chemical constituent, said method comprising flowing said chemical constituent into an optical detector and measuring said chemical constituent without ever contacting a fluid valve with said abrasive slurry particles.

23. A system for measuring a chemical constituent of an opaque slurry comprising opaque slurry particles and said chemical constituent, said method comprising:
    a separator for separating said slurry particles from said chemical constituent, and said separator comprising a slurry region and a chemical constituent region;
    an optical detector; and
    a flow control system for controlling flow of said chemical constituent from said chemical constituent region to said optical detector.

24. A system as in claim 23 wherein said separator comprises a filter.

25. A system as in claim 24 wherein said separator comprises a cross-flow filter.

26. A system as in claim 24 wherein said separator comprises a filter selected from the group consisting of a ceramic filter and an inert polymer membrane filter.

27. A system as in claim 26 wherein said filter includes a permeate port located at the top of said filter.

28. A system as in claim 27 wherein said optical detector includes a flow cell and said flow control system includes a chemical constituent conduit connected between said permeate port and the bottom of said flow cell.

29. A system as in claim 23 wherein said flow control system includes a pressure bleed port.

30. A system as in claim 29 wherein said flow control system further includes a valve located between said optical detector and said pressure bleed port.

31. A system as in claim 23 wherein said flow control system includes a pressure source and a first valve.

32. A system as in claim 31 wherein said first valve is located between said pressure source and said optical detector.

33. A system as in claim 32 and further including a second valve located between said pressure source and said separator.

34. A system as in claim 32 wherein said first valve is located between said pressure source and said separator.

35. A system as in claim 23 wherein said flow control system includes a reservoir connected to said optical detector.

36. A system as in claim 35 and further including: a chemical constituent return conduit; a first valve connected between said separator and said optical detector; a second valve connected between said optical detector and said reservoir; and a third valve connected between said reservoir and said chemical constituent return conduit.

37. A system as in claim 36 and further including a fourth valve located between said reservoir and said separator.

38. A system as in claim 35 and further including a liquid level sensor connected to said reservoir.

39. A system as in claim 23 wherein said optical detector comprises a spectrometer.

40. A system as in claim 23 wherein said flow control system further controls flow of said separated slurry particles from said slurry region, and said control system includes a conduit adapted to connect said separator to a day tank of a slurry distribution system.

41. A system for measuring a chemical constituent of an opaque slurry comprising opaque slurry particles and said chemical constituent, said systems comprising:
    a filter including a filter input port, a slurry retentate region, and a chemical constituent permeate region;
    an optical detector; and
    a flow control system comprising: a conduit connecting said chemical constituent permeate region and said optical detector, and a pressure bleed port connected to said optical detector.

42. A system as in claim 41 wherein said optical detector comprises a spectrometer.

43. A system as in claim 42 wherein said filter is selected from the group consisting of a ceramic filter and an inert polymer membrane filter.

* * * * *